United States Patent
Matsunaga et al.

(10) Patent No.: US 9,149,249 B2
(45) Date of Patent: Oct. 6, 2015

(54) ULTRASOUND IMAGE DIAGNOSIS APPARATUS AND A CONTROL METHOD FOR MEASURING DIAGNOSIS PARAMETERS

(75) Inventors: Satoshi Matsunaga, Tochigi-ken (JP); Osamu Nakajima, Tochigi-ken (JP); Koichiro Kurita, Tochigi-ken (JP); Masaru Ogasawara, Tochigi-ken (JP); Go Tanaka, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 250 days.

(21) Appl. No.: 12/827,805

(22) Filed: Jun. 30, 2010

(65) Prior Publication Data
US 2010/0331693 A1 Dec. 30, 2010

(30) Foreign Application Priority Data
Jun. 30, 2009 (JP) ................................ P2009-155324

(51) Int. Cl.
| A61B 8/00 | (2006.01) |
| A61B 8/06 | (2006.01) |
| A61B 8/02 | (2006.01) |
| A61B 8/08 | (2006.01) |

(52) U.S. Cl.
CPC ... *A61B 8/06* (2013.01); *A61B 8/02* (2013.01); *A61B 8/4281* (2013.01); *A61B 8/488* (2013.01); *A61B 8/5238* (2013.01)

(58) Field of Classification Search
USPC ........................ 600/441, 443, 445, 453, 454
See application file for complete search history.

(56) References Cited

U.S. PATENT DOCUMENTS

| 5,782,766 | A  | * | 7/1998 | Weng et al. ................... 600/443 |
| 6,328,693 | B1 | * | 12/2001 | Miyatake et al. ............. 600/437 |
| 6,582,367 | B1 | * | 6/2003 | Robinson et al. ............. 600/443 |
| 6,884,216 | B2 | * | 4/2005 | Abe et al. ..................... 600/440 |
| 2007/0282203 | A1 | * | 12/2007 | Baba et al. ..................... 600/453 |
| 2011/0079082 | A1 | * | 4/2011 | Yoo et al. ........................ 73/632 |

FOREIGN PATENT DOCUMENTS

| JP | 5-228144 | | 9/1993 |
| JP | 2004-229958 | A | 8/2004 |
| JP | 2008-279110 | A | 11/2008 |

OTHER PUBLICATIONS

Notice of Rejection Reasons issued Mar. 28, 2014 in Japanese Patent Application No. 2009-155324 (with English translation).
Office Action issued Jul. 16, 2013, in Japanese Patent Application No. 2009-155324 with English translation.

* cited by examiner

*Primary Examiner* — Long V Le
*Assistant Examiner* — Ellsworth Weatherby
(74) *Attorney, Agent, or Firm* — Oblon, McClelland, Maier & Neustadt, L.L.P.

(57) ABSTRACT

An ultrasound image diagnosis apparatus that can display image data acquired at a plurality of measuring positions in panoramic image data and display measured results of diagnosis parameters for each of the measuring positions of the panoramic image data The panoramic image data is generated by combining a plurality of reference image data generated at a plurality of diagnosis target positions. The plurality of measuring positions is designated based on the latest reference image data composing the panoramic image data. Based on Doppler signals acquired through ultrasound transmissions and receptions to and from the plurality of measurement positions, image data is generated.

14 Claims, 9 Drawing Sheets

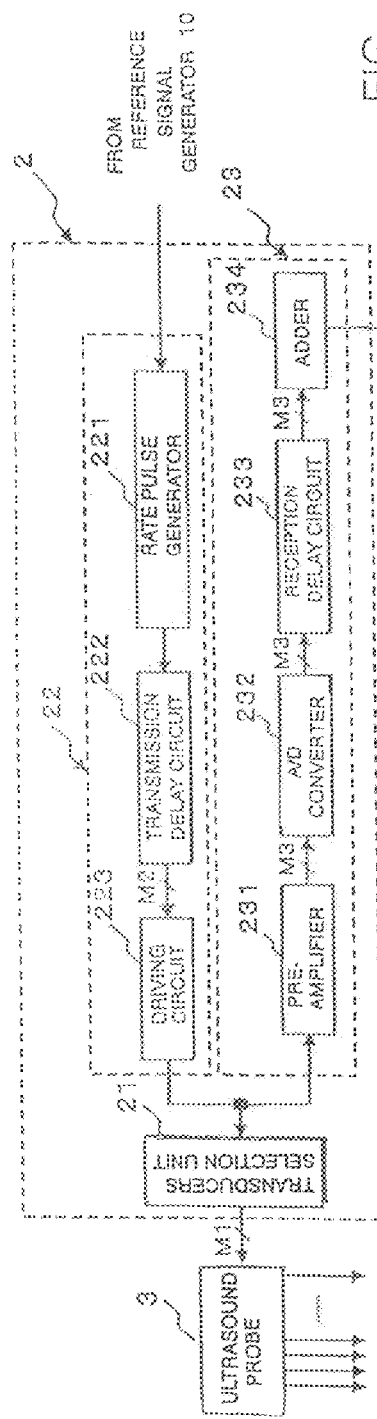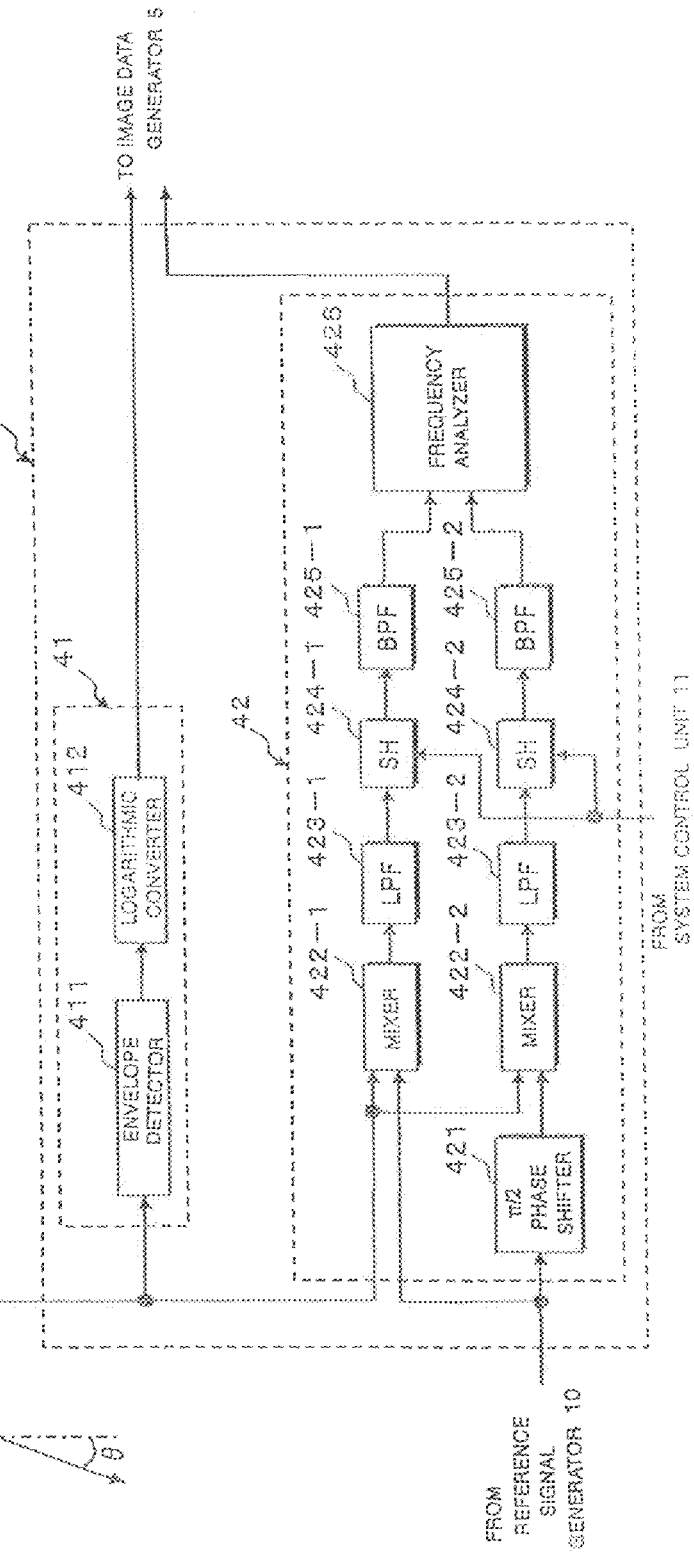
FIG. 2

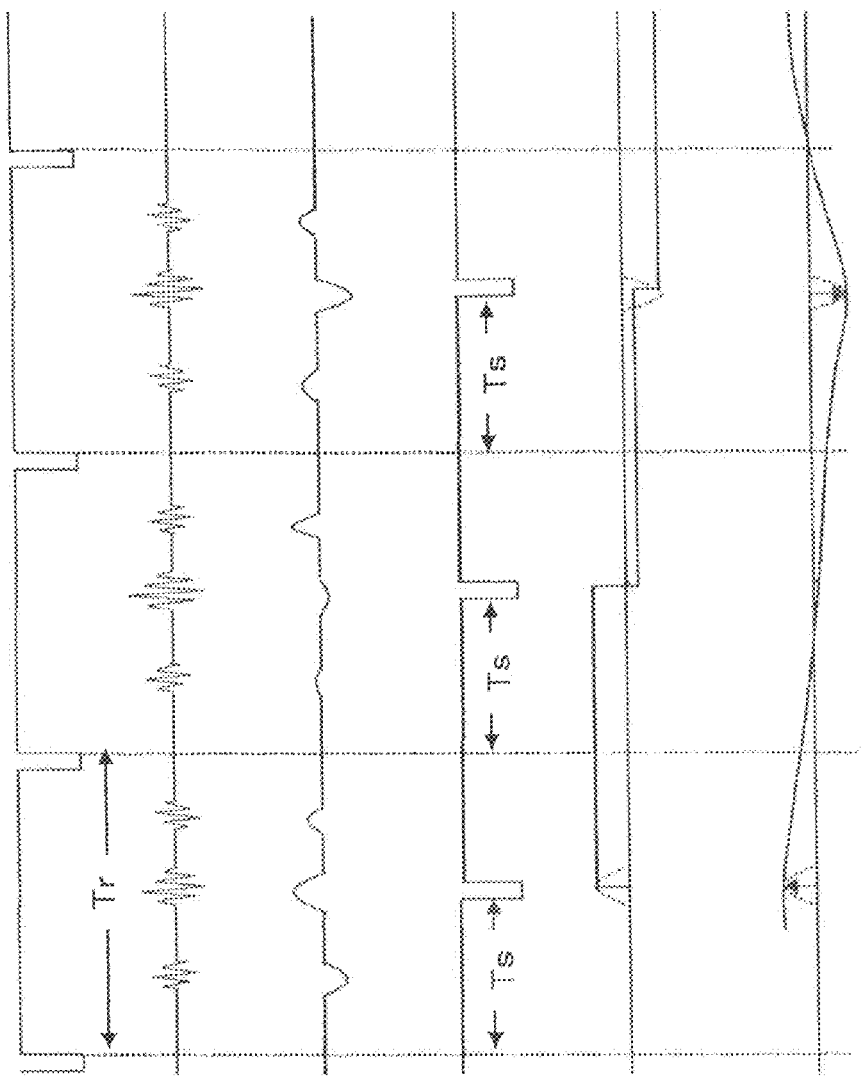
FIG. 4A REFERENCE SIGNALS
FIG. 4B RATE PULSES
FIG. 4C RECEIVING SIGNALS
FIG. 4D ORTHOGONAL PHASE DETECTION OUTPUT (OUTPUT OF LPF423)
FIG. 4E SAMPLE GATE PULSES (OUTPUT OF SYSTEM CONTROLLER 11)
FIG. 4F DOPLLER SIGNALS (OUTPUT OF SH424)
FIG. 4G DOPLLER SIGNALS (OUTPUT OF BFP425)

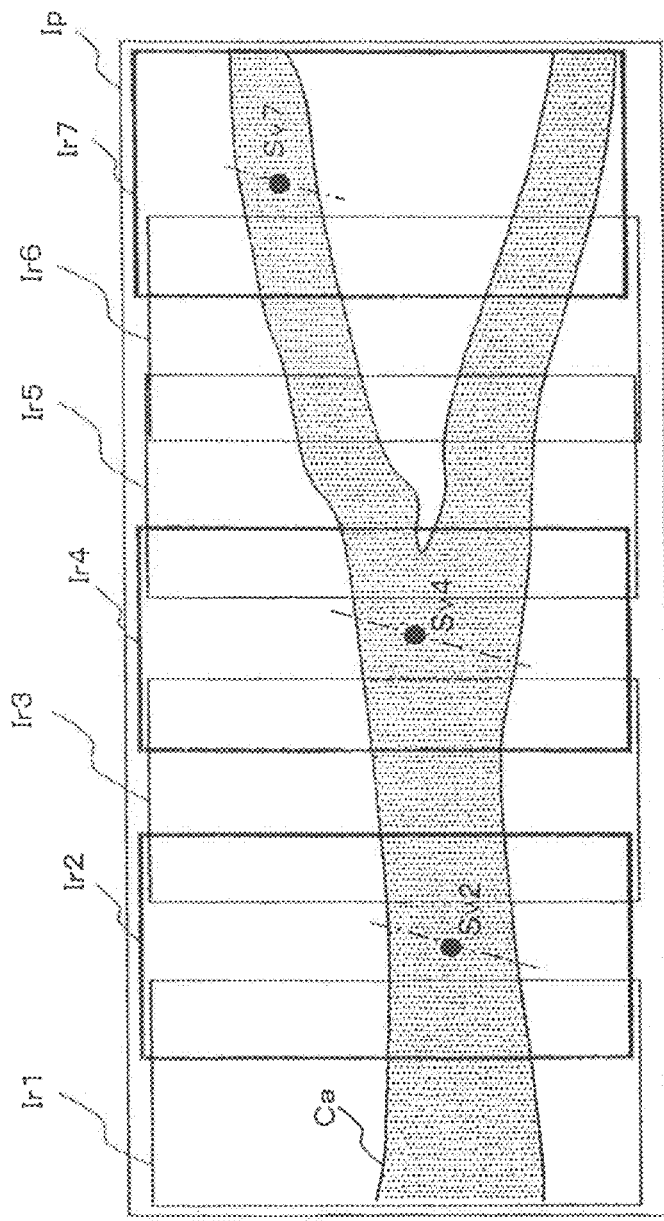
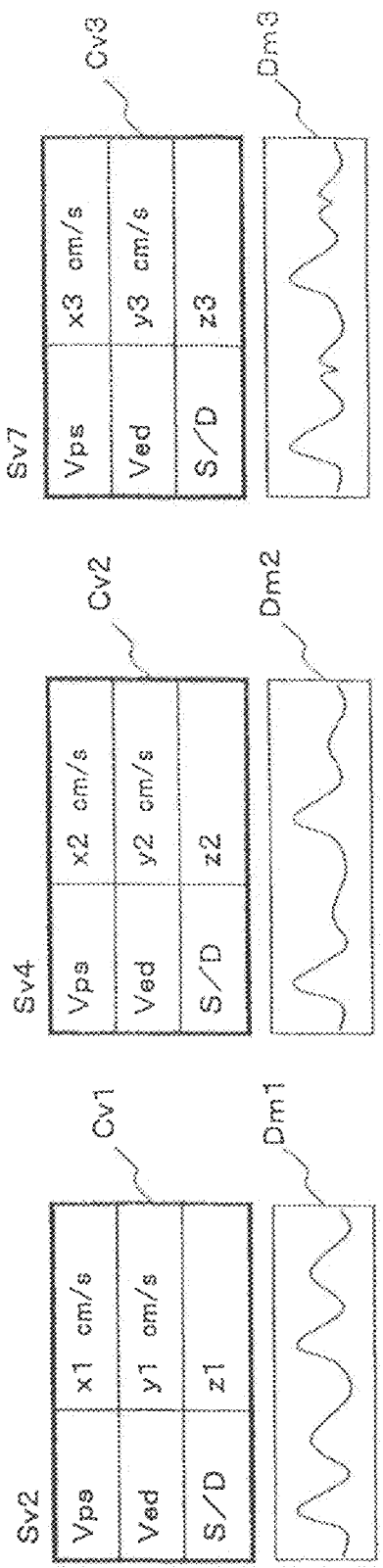
FIG. 8

ULTRASOUND IMAGE DIAGNOSIS APPARATUS AND A CONTROL METHOD FOR MEASURING DIAGNOSIS PARAMETERS

CROSS-REFERENCE TO RELATED APPLICATIONS

This application claims the benefit of priority under 35 U.S.C §119(a) from Japanese Patent Application No. 2009-155324, filed on Jun. 30, 2009, the contents of which are expressly incorporated herein by reference in their entirety.

BACKGROUND OF THE INVENTION

A. Field of the Invention

The present invention relates to an ultrasound image diagnosis apparatus and control method thereof for measuring diagnosis parameters, and more particularly to an ultrasound image diagnosis apparatus and control method thereof that displays panoramic image data showing wide scope figure data associated in time series with a plurality of measured image data and/or measured values acquired from the measured data and showing functional data.

B. Background of the Invention

An ultrasound image diagnosis apparatus typically transmits ultrasounds via ultrasound transducers installed in an ultrasound probe to an object, such as a patient, and receives the reflected ultrasounds (echo signals) which show differences in the acoustic impedances of the object's organs enabling the display of an image of the organ on a monitor. Since the ultrasound image diagnosis apparatus can easily obtain two dimensional images in a real time from the simple touching of an ultrasound probe to a patient body surface, this device is widely used for diagnosing various statuses of a patient's body.

Ultrasound diagnosis methods for acquiring living body data through reflection waves from tissues or blood cells in a living body have been rapidly developing due to significant technology developments such as the ultrasound pulses reflection method and the ultrasound Doppler method. As a result of the development of these technologies, a B mode method for acquiring B mode image data and a color Doppler method for acquiring color Doppler image data are now available for ultrasound image diagnosis.

Further, Doppler spectrum methods and M mode methods have also been developed. In these methods, reception signals are acquired by performing transmissions/receptions in a prescribed direction for an object. The Doppler spectrum method generates frequency spectrum of Doppler signal components (hereinafter, referred to as "spectrum data") by processing the receiving signals. The Doppler spectrum method is able to quantitatively and accurately measure the speed of the bloodstream in a measuring region in a prescribed direction by measuring temporal changes of the spectrum data. The M mode method is able to quantitatively evaluate vital functions of living body tissues by measuring temporal changes in reflection intensity (B mode data) of the receipion signals acquired in a prescribed direction.

The M mode image data acquired through the M mode method is generated by successively arranging a time series B mode data in a time axis direction. The time series B mode data is acquired through repetitions of a plurality of ultrasound transmissions/receptions in the same direction to/from an object. Thus, the M mode image data is usually shown as a distance to a reflection body on a longitudinal axis with time on a horizontal axis. The amplitude of the B mode data is shown by brightness.

In the Doppler spectrum method, a plurality of ultrasound transmissions and receptions in the same direction with respect to an object are repeated at a prescribed interval. The Doppler signals are detected by performing orthogonal phase detections on the ultrasound echo waves reflected from moving reflection bodies, such as blood cells, using a reference signal that has a frequency that is substantially equal to the center frequencies of ultrasound pulses. The spectrum data is then generated by performing a frequency analysis of the Doppler signal extracted from the Doppler signals through a range gate in a desired measurement position. Further, spectrum image data is generated by successively arranging a plurality of spectrum data that is time sequentially acquired at the measurement positions, in a time axis direction. Moreover, the spectrum image data generated trough the Doppler spectrum method is usually shown as a longitudinal axis for frequency and a horizontal axis for time. The power (strength) of each frequency components is shown by brightness (tone).

To correctly set up the range gate at a measuring position on an object, the range gate is set up after monitoring the B mode image data or the color Doppler image data (hereinafter, the image data for setting the range gate is collectively referred to as "reference image data"), and a measurement marker showing a position of the range gate is displayed in an overlapping manner on the reference image data.

Conventionally, a display method has been proposed for displaying spectrum image data generated at the measuring position and various diagnosis parameters measured based on the generated spectrum image data together with the reference image data having overlapped measurement markers (for instance, see Japanese Patent Application Publication 2005-81081).

In the conventionally proposed method, a maximum frequency fp is initially detected for each of a plurality of spectrum data acquired in a time series. Based on a trace waveform (trend waveform) indicating temporal changes of the plurality maximum frequencies fp, a peak of systolic (Ps) and an end of diastolic (Ed) of a heart are detected. Then, based on the peak of systolic (Ps) and the end of diastolic (Ed), measurements of diagnosis parameters for peripheral blood vessels are performed.

Such generations of the trace waveforms, detections of the peak of systolic (Ps) and the end of diastolic (Ed), or measurements of the diagnosis parameters have been, in the past, manually performed using freeze spectrum image data. However, recently, a method for automatically measuring diagnosis parameters using spectrum image data displayed in a real time has been developed (for instance, see U.S. Pat. No. 5,628,321).

However, in these conventional methods, image data is acquired in a narrow region of one frame. As a result, when monitoring the acquired reference image data, only one measuring position is designated as an efficient position for a diagnosis of the object. Spectrum image data is generated at the designated measuring position, and diagnosis parameters are measured based on the spectrum image data. Then both the generated spectrum image data and the measured diagnosis parameters are displayed with the reference image data. Consequently, observing a plurality of bloodstream data in a blood vessel passing through a wide range covered by a plurality frames, such as a carotid artery, having a plurality of measuring positions, has been difficult. Thus, while the plurality of measured data is somewhat displayable, the display of the measured data corresponding to each of the plurality of measuring positions has not been achieved. Thus, it has been nearly impossible to observe comparison data between upstream data and downstream data of the bloodstream in a blood vessel, or to observe comparison data between bloodstream data before and after a branching of a blood vessel based on the reference image data. Accordingly, after finishing desired measurements, a laboratory technician has conventionally illustrated identifying relationships between each measured value and each measuring position. Consequently, such operation has severely imposed strain on the operator, such as a doctor or a laboratory technician. Further, the conventional method has reduced diagnosis accuracy and throughput efficiency of the diagnosis.

SUMMARY OF THE INVENTION

The present invention addresses these and other problems and drawbacks and provides an ultrasound image diagnosis apparatus and a control method for measuring diagnosis parameters that can easily and accurately generate a plurality of measured image data at a plurality of designated measuring positions, and measure diagnosis parameters based on the plurality of measured image data a wider region provided by panoramic image data.

One embodiment of the invention includes an ultrasound image diagnosis apparatus that measures diagnosis parameters based on image data acquired through ultrasound transmissions and receptions along prescribed directions with respect to an object, the ultrasound image diagnosis apparatus comprising:

an ultrasound probe including a plurality of transducers configured to transmit and receive ultrasound pulses and ultrasound echo waves to and from the object;

a transmission/reception unit configured to supply driving signals to the plurality of transducers for transmitting the ultrasound pulses along the prescribed directions and to perform phase compensation/summation on a plurality of reception signals acquired from the plurality of transducers;

an ultrasound data generating unit configured to generate both ultrasound data in a reference mode and ultrasound data in a measurement mode by processing the phase compensated/summed receiving signals;

a reference image data generating unit configured to generate a reference image data based on ultrasound data in the reference mode acquired through ultrasound transmission/reception along the prescribed directions with respect to the object;

a panoramic image data generating unit configured to generate a panoramic image data from the reference image data successively generated in accordance with movements of the ultrasound probe;

a measured image data generating unit configured to generate measured image data based on ultrasound data acquired in the measurement mode through ultrasound transmission/reception at a plurality of measurement positions designated in the panoramic image data;

a diagnosis parameters measuring unit configured to measure the diagnosis parameters based on the measured image data; and a display unit configured to display the panoramic image data together with at least one of the measured image data and the measured results of the diagnosis parameters.

Another aspect of an embodiment of the invention is a control method for measuring diagnosis parameters of an ultrasound image diagnosis apparatus that measures diagnosis parameters based on image data acquired through ultrasound transmission/reception along prescribed directions with respect to an object, the measurement controlling method comprising:

supplying driving signals to a plurality of transducers in an ultrasound probe that transmit ultrasound pulses along the prescribed directions and performing phase compensation/summation on a plurality of receiving signals acquired from the plurality of transducers;

generating both ultrasound data in a reference mode and ultrasound data in a measurement mode by processing the phase compensated/summed receiving signals;

generating reference image data based on ultrasound data obtained in the reference mode acquired through ultrasound transmission/reception along the directions with respect to the object;

generating panoramic image data from a plurality of the reference image data successively generated in accordance with movements of the ultrasound probe;

generating measured image data based on ultrasound data acquired in the measurement mode through ultrasound transmission/reception at a plurality of measurement positions designated in the panoramic image data;

measuring the diagnosis parameters based on the measured image data; and displaying the panoramic image data together with at least one of the measured image data or the measured results of the diagnosis parameters.

According to the embodiments of the present invention, it becomes possible to easily and accurately generate a plurality of image data and measure diagnosis parameters at respective measuring positions designated in the panoramic image data displayed in a wider range under monitoring the panoramic image data,. Accordingly, diagnosis accuracy and efficiency can be significantly improved. Further, the burden to the operators during ultrasound examinations is reduced.

BRIEF DESCRIPTION OF THE DRAWINGS

The accompanying drawings, which are incorporated in and constitute part of this specification, illustrate various embodiments and/or features of the present invention, and together with the description, serve to explain embodiments of the present invention. Where possible, the same reference number will be used throughout the drawings to describe the same or like parts. In the drawings:

FIG. 2 is a block diagram illustrating the transmission/reception unit and the ultrasound data generating unit provided in the ultrasound diagnosis apparatus shown in FIG. 1;

FIGS. 4A-4G illustrate time charts showing basic operations of the spectrum data generating unit in the ultrasound diagnosis apparatus shown in FIG. 1;

FIG. 8 illustrates an example of display data in the ultrasound diagnosis apparatus according to one embodiment of the invention;

DESCRIPTION OF PREFERRED EMBODIMENTS

In one embodiment of the present invention broad range image data (hereinafter referred to as "panoramic image data") is generated from a plurality of reference image data acquired at a plurality of diagnosis target positions on an object. The plurality of reference image data is acquired by successively moving an ultrasound probe having a plurality of transducers arrayed in a single dimension. Based on the latest reference image data included in the panoramic image data, a measuring position of the bloodstream data is designated. Then, image data is generated based on Doppler signals acquired through ultrasound transmission/reception at the designated measuring position. Diagnosis parameters are measured using the image data. The image data acquired at each of the designated plurality of bloodstream data measuring positions and the measurement results of the diagnosis parameters are displayed. In addition, the image data and the measurement results are displayed in correspondence with each of the measuring positions of the bloodstream data in the panoramic image data.

In the following embodiment, as an example case, B mode image data is generated as the reference image data, and spectrum image data is generated as the measured image data (hereinafter, simply referred to as "image data"). Of course, it is also possible to use color Doppler image data or B mode image data overlapped on color Doppler image data, as the reference image data. It is also possible to use, as the image data, M mode image data which indicates temporal changes of B mode data. In the present embodiment, while the reference image data is generated based on the receiving signals acquired through linear scan type ultrasound transmissions and receptions, the reference image data may also be acquired through sector scan type or convex scan type ultrasound transmissions and receptions.

Figure 1:
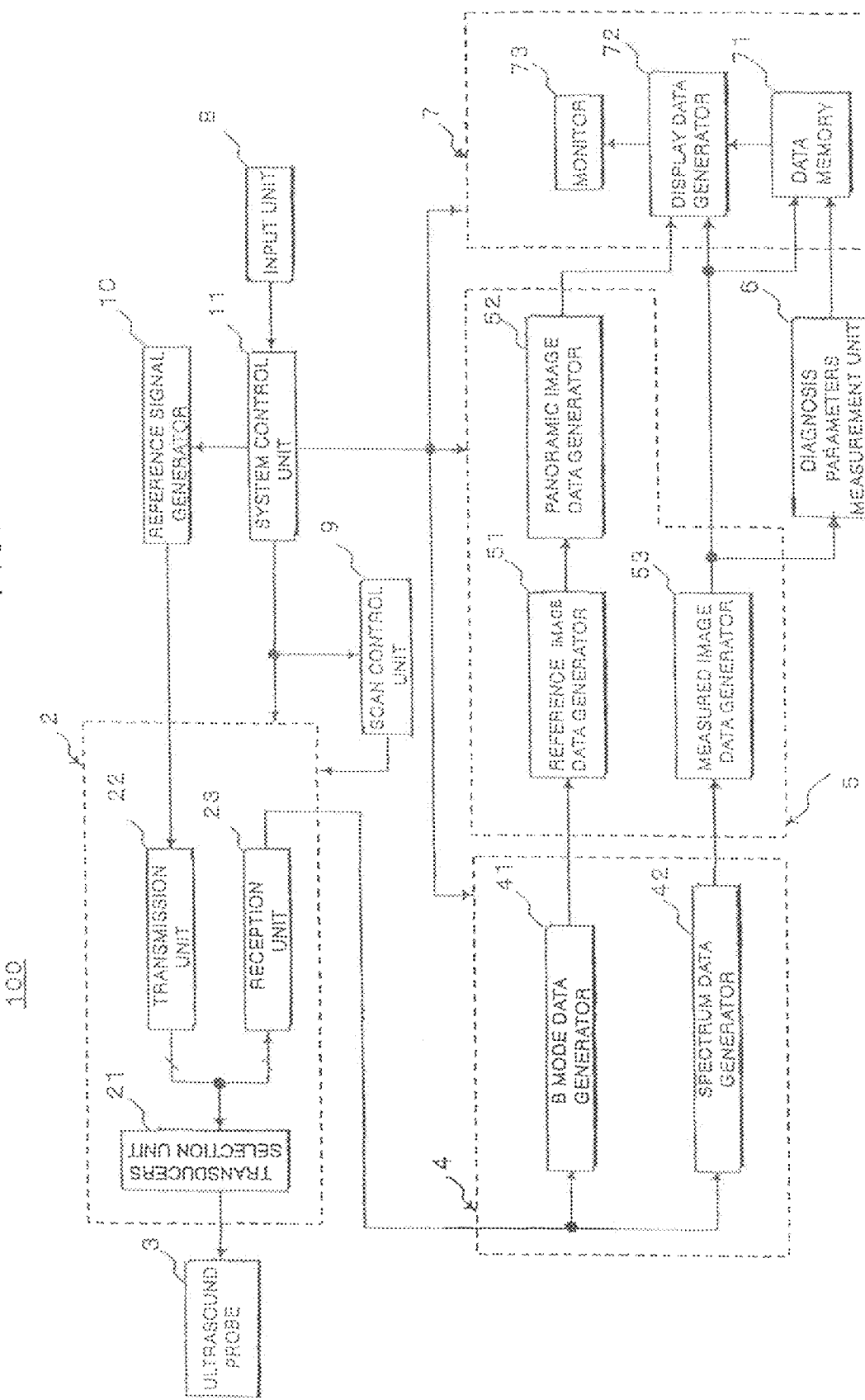
FIG. 1 is a block diagram illustrating an ultrasound diagnosis apparatus according to an embodiment of the present invention.

FIG. 1 is a block diagram illustrating an ultrasound diagnosis apparatus according to one embodiment of the present invention. The ultrasound diagnosis apparatus 100 includes a transmission/reception unit 2, an ultrasound probe 3, an ultrasound data generating unit 4, an image data generating unit 5 and a diagnosis parameters measuring unit 6. The ultrasound probe 3 includes a plurality of transducers for transmitting ultrasound pulses (transmission type ultrasounds) to an examination target region of an object, e.g., a neck portion, and converting ultrasound echo waves (receiving type ultrasounds), acquired through the transmission, to electrical signals (receiving type signals). The transmission/reception unit 2 supplies driving signals for transmitting ultrasound pulses in prescribed directions to an examination target region and performs phase compensations and summations of received signals for a plurality channels acquired through the plurality of transducers. The ultrasound data generating unit 4 generates B mode data and spectrum data by processing the phase compensated and summed received signals. The image data generating unit 5 generates reference image data and panoramic image data by arranging the B mode data acquired by the ultrasound data generating unit 4 for various ultrasound transmission/reception directions. Image data is generated by arranging the spectrum data acquired in the ultrasound data generating unit 4 along a time axis direction. The diagnosis parameters measuring unit 6 measures various diagnosis parameters based on the image data.

The ultrasound diagnosis apparatus 100 further includes a display unit 7, an input unit 8, a scan control unit 9, a reference signal generating unit 10 for generating a reference signal, and a system control unit 11. The display unit 7 displays the panoramic image data by overlapping or composing the measured image data and the measured results of diagnosis parameters. The input unit 8 inputs object data and various command signals. Further the input unit 8 sets up image data generating conditions and designates measurement positions of bloodstream data on the panoramic image data. The scan control unit 9 controls ultrasound transmission/reception directions in a reference mode for generating reference image data and in a measurement mode for generating image data. The system control unit 11 may entirely control each of the above-discussed units. The system control unit 11 may include a central processing unit.

The ultrasound probe 3 includes a plurality of one dimensionally (1-D) arrayed transducers M1 (not shown) in a tip portion. Ultrasound transmissions and receptions are performed by touching the tip portion of the ultrasound probe 3 to a body surface of an object. The transducer is made of an electrical acoustic conversion element that converts the transmission driving signals (transmission type ultrasounds) to ultrasound pulses and that converts the ultrasound echo waves into the ultrasound reception signals. The plurality of transducers are coupled to the transmission/reception unit 2 through a plurality channels of a cable.

FIG. 2 illustrates the configuration of the transmission/reception unit 2 and the ultrasound data generating unit 4 in the ultrasound diagnosis apparatus shown in FIG. 1. The transmission/reception unit 2 includes a transducer selection unit 21, a transmission unit 22, and a reception unit 23. The element selection unit 21 selects a plurality of transmission transducers M2 and a plurality of reception transducers M3 among the plurality of transducers M1 provided in the ultrasound probe 3. The transmission unit 22 supplies driving signals, each having a prescribed transmission delay time and driven amplitude, to the plurality of transmission transducers M2 for a prescribed direction. The reception unit 23 performs phase compensations and summations of the plurality of receiving signals acquired from the plurality of reception transducers M3 from the prescribed directions.

During transmission, the elements selection unit 21 selects a plurality of adjoined transducers M2, among the plurality M1 of transducers provided in the ultrasound probe 3, as a transmission transducer group. The selection of the transmission transducer group is based on element selection control signals supplied from the scan control unit 9. During reception, the transducer selection unit 21 selects a plurality of adjoined transducers M3 among the plurality M1 of transducers as a reception transducer group. The elements selection unit 21, for instance, includes a plurality of electronic switching circuits corresponding to the plurality of transducers M1 in the ultrasound probe 3, and selects the transmission transducer group and the reception transducer group by controlling the switching circuits. The selected transmission transducer group is connected to the transmission unit 22. The selected reception transducer group is connected to the reception unit 23. The selection of the transducer groups is performed so that a center position of the transmission transducer group substantially coincides with a center position of the reception transducer group. In a reference mode, ultrasound transmissions and receptions, i.e., linear scans, are performed at a perpendicular direction θ=0 to an array direction of transducers by successively shifting the transmission transducer group and the reception transducer group in the array direction of the transducers at a rate interval (repetition cycle of transmission type ultrasounds). In a measurement mode, ultrasound transmissions and receptions are performed along a crossing direction θd to a bloodstream data measurement position by fixing the transmission transducer group and reception transducer group at an appropriate position with respect to the array direction.

The transmission unit 22 includes a rate pulse generator 221, a transmission delay circuit 222 and a drive circuit 223. The rate pulse generator 221 generates rate pulses for determining a repetition cycle of the transmission type ultrasounds by dividing the reference signals supplied from the reference signal generating unit 10 shown in FIG. 1. The transmission delay circuit 222 is constructed from independent delay circuits the number of independent delay circuits being the same as the number of transmission transducers M2. The transmission delay circuit 222 provides a convergence delay time for converging transmission type ultrasounds at a prescribed depth and a deflection delay time for transmission type ultrasounds in a prescribed direction θd with respect to the rate pulses supplied from the rate pulse generator 221. The drive circuit 223 includes the same number of independent drive circuits as the transmission delay circuit 222. The drive circuit 223 generates driving signals based on the rate pulses delayed by the transmission delay circuit 222. Ultrasounds are transmitted into an object by supplying the driving signals to the plurality of transmission transducers M2 selected by the elements selection unit 21.

The reception unit 23 includes a plurality of pre-amplifiers 231 corresponded to the plurality of reception transducers M3 selected by the elements selection unit 21, an A/D converter 232, reception delay circuits 233, and an adder 234. The plurality of reception signals supplied from the reception transducers M3 through the pre-amplifiers 231 are converted to digital data in the A/D converter 232 and supplied to the reception delay circuit 233.

The reception delay circuit 233 provides a convergence delay time for converging reception type ultrasounds from a prescribed depth and a deflection delay time for setting a reception directivity along a prescribed direction θd for each of the plurality of reception signals M3 outputted from the A/D converter 232. The adder 234 adds the reception signals supplied from the reception delay circuit 233. Thus, phase compensations and summations are performed on the reception signals acquired along the direction θ=0 or θ=θd by using the reception delay circuit 233 and the adder 234.

In the case of a linear scan in a reference mode for performing ultrasound transmissions and receptions in a direction θ=0, the transmission delay circuit 222 and the reception delay circuit 233 only supply a convergence delay time for converging transmission type ultrasounds at a prescribed depth and a convergence delay time for converging reception type ultrasounds from the prescribed depth.

Figure 3A:
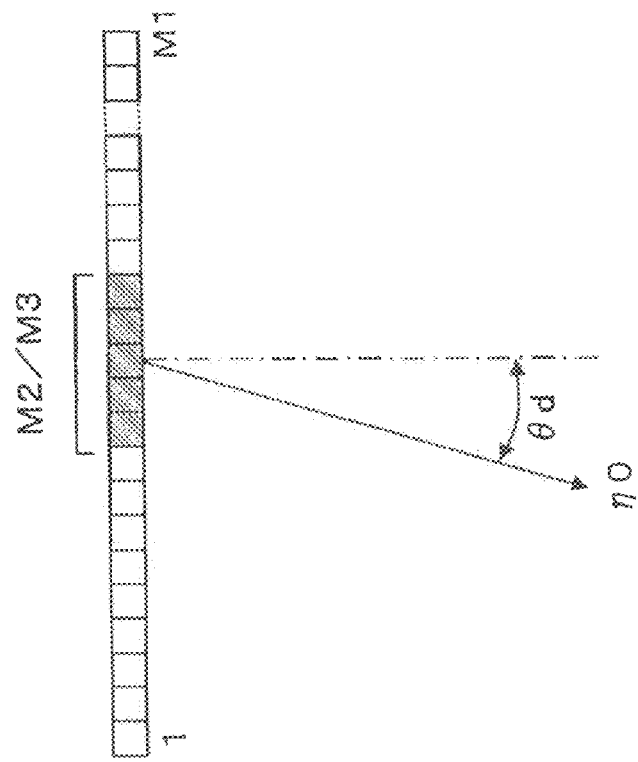
FIGS. 3A and 3B illustrate a reference mode of the ultrasound diagnosis apparatus shown in FIG. 1 and ultrasound transmission/reception directions in a measurement mode.
Figure 3B:
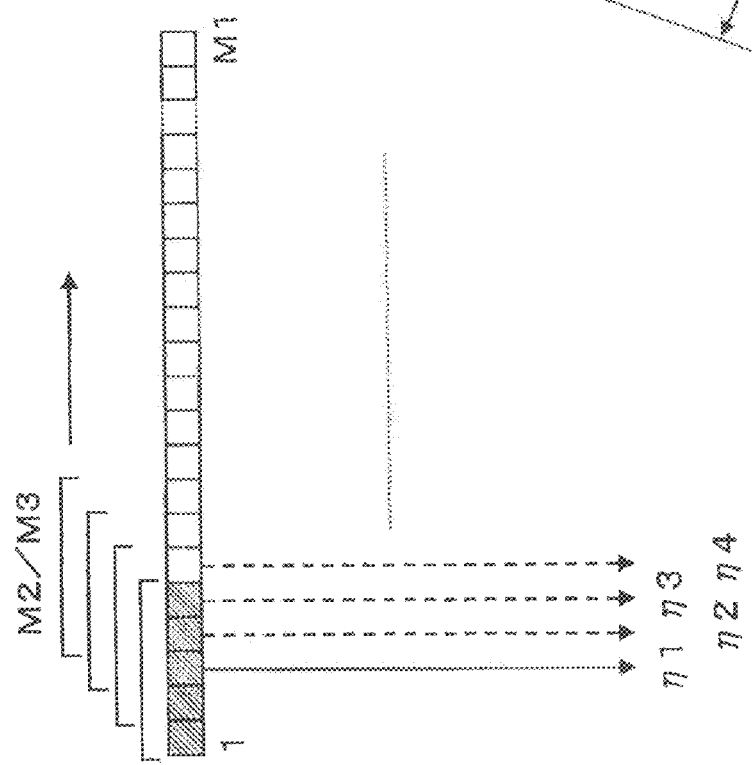

FIGS. 3A and 3B illustrate ultrasound transmission/reception directions in a reference mode and a measurement mode, respectively. In FIGS. 3A and 3B, the highlighted elements correspond to a plurality of transmission transducer groups M2 and a plurality of reception transducer groups M3 that are selected among the plurality of transducers M1 provided in the ultrasound probe 3 for one ultrasound transmission and reception. In one example, the number of elements in a transmission transducer group equals the number of elements in the reception group (M2=M3). However, other configurations are available.

FIG. 3A illustrates ultrasound transmissions and receptions in the reference mode of a linear scan method for acquiring reference image data. For instance, at a first rate period, an ultrasound transmission/reception along a direction η1 is performed by selecting and driving a plurality of transducers M2 starting at element "1". At a second rate period, ultrasound transmission/reception along a direction η2 is performed by selecting and driving a plurality of transducers M2+1 starting at element "2". By repeating the similar steps, with successively shifting the transmission transducer group and the reception transducer group in an array direction for the transducer at a rate interval, ultrasound transmissions and receptions are performed along a direction θ=0 perpendicular to the array direction.

FIG. 3B illustrates ultrasound transmissions and receptions in a measurement mode for acquiring image data. In this case, a plurality of transmission transducer groups M2 and a plurality of reception transducer groups M3 located at an appropriate position for performing ultrasound transmissions to and receptions from a bloodstream data measurement position are selected from the plurality of transducers M1. By driving these transducer groups, ultrasound transmissions and receptions are performed along a prescribed direction η0 (θd).

When acquiring the image data, an acquisition of reference image data is performed as well in order to confirm whether the ultrasound transmission and reception direction η0 shown in FIG. 3B is appropriate to the bloodstream data measurement position. In such a case, ultrasound transmission and reception, in a measurement mode along a direction η0, is performed after performing ultrasound transmission and reception in a reference mode along a direction η1. Moreover, after the ultrasound transmission and reception in the reference mode along a direction η2, ultrasound transmission and reception in the measurement mode along the direction η0 is performed. Thus, by successively performing ultrasound transmissions and receptions along the directions η1, η0, η2, η0, η3, η0 . . . , monitoring of ultrasound transmission and reception directions in an acquisition of image data can be made under observation of the reference image data.

As mentioned above, in the reference mode, the linear scan method shown in FIG. 3A is typically applied to monitor vascular structures in a high resolution. In the measurement mode, the deflection method shown in FIG. 3B for deflecting the ultrasound transmission and reception direction in a direction θd is used to measure Doppler signals with high sensitivity.

Referring to FIG. 2, the ultrasound data generating unit 4 includes a B mode data generating unit 41 and a spectrum data generating unit 42. The B mode data generating unit 41 generates B mode data by processing receiving signals outputted from the adder 234 in the reception unit 23. The spectrum data generating unit 42 generates frequency spectrum data of the Doppler signal (hereinafter, "Doppler spectrum data") by detecting Doppler signals through orthogonal detection of the receiving signals.

The B mode data generating unit 41 includes an envelope detector 411 and a logarithmic converter 412. The envelope detector 411 detects an envelope of the phase compensated and summed reception signals supplied from the adder 234 in the reception unit 23. The logarithmic converter 412 generates B mode data by logarithmically converting the detected reception signals.

The spectrum data generating unit 42 includes a π/2 phase shifter 421, mixers 422-1 and 422-2, low-pass filters (LPF) 423-1 and 423-2, sample hold circuits 424-1 and 424-2, band-pass filters (BPF) 425-1 and 425-2 and a frequency analyzer 426. The spectrum data generating unit 42 detects Doppler signals by orthogonally detecting the reception signals supplied from the adder 234 in the reception unit 23, and performs frequency analysis on the acquired Doppler signals.

FIGS. 4A-4G are time charts showing basic operations in the spectrum data generating unit 42. FIGS. 4A-4G respectively illustrate a frame format of output signals from each of the units in the spectrum data generating unit 42. FIG. 4A illustrates reference signals of the reference signal generating unit 10. The reference signals have a frequency which is substantially equal to the center frequency of the reception signals. FIG. 4B illustrates rate pulses outputted from the rate pulses generator 211. FIG. 4C illustrates reception signals outputted from the adder 234 in the reception unit 23. The reception signals outputted from the adder 234 are inputted into the first input terminal of the spectrum data generating unit 42 and the first input terminal of the mixers 422-1 and 422-2, respectively. The reference signals (FIG. 4A) from the reference signal generating unit 10 are directly supplied to the second input terminal of the mixer 422-1. The phase reference signal from the reference signal generating unit 10 is shifted by 90 degrees through the $\pi/2$ phase shifter 421 and supplied to the second input terminal of the mixer 422-2. Each output from the mixers 422-1 and 422-2 is respectively supplied to the LPFs 423-1 and 423-2, and by eliminating the sum component of a frequency of the reception signals outputted from the adder 234 and a frequency of the reference signals supplied from the reference signal generating unit 10, the difference component isolated and output as Doppler signals (FIG. 4D).

As illustrated in FIG. 4E, the system control unit 11 divides the reference signals from the reference signal generating unit 10 and generates sampling pulses (range gate pulses). Then, the Doppler signals outputted from the LPSs 423-1 and 423-2 and the range gate pulses are supplied to each of the sample hold circuits (SH) 424-1 and 424-2. As illustrated in FIG. 4F, only Doppler signals reflected from a region of interest positioned at a distance corresponding to the generation timing of the range gate pulses are taken into account. The range gate pulses are generated after a prescribed delay time Ts from the rate pulses period Tr (FIG. 4B) indicating radiation timing of the transmission type ultrasounds. The generation timing of the range gate pulses can be manually set up in the input unit 8.

Thus, a range gate can be set at a measuring position of the bloodstream data positioned at a distance Lg from the ultrasound probe 3 by changing the delay time Ts. Thus, an operator can selectively detect a Doppler signal from the measuring position of the bloodstream data set up in the range gate. The delay time Ts and the distance Lg from the ultrasound probe 3 to the bloodstream data measurement position are related according to the equation $2Lg/C=Ts$, where C is a sound velocity of living body tissue.

FIG. 4F illustrates stair-like noise components placed on the Doppler signals of the bloodstream data measurement position outputted from the sample hold circuits 424-1 and 424-2. As illustrated in FIG. 4G, the Doppler signals are eliminated through the band-pass filters (BPFs) 425-1 and 425-2. The smoothed Doppler signals are supplied to the frequency analyzer 426. The BPFs 425-1 and 425-2 also have a function for clearing out extra clutter signals from the Doppler signals which are produced due to blood vessels or living body tissues having a slower moving speed than the bloodstream speed.

In FIG. 2, the frequency analyzer 426 includes a calculation circuit and a memory circuit (both are not shown). The memory circuit stores the complex Doppler signal outputted from the BPFs 425-1 and 425-2. The calculation circuit generates spectrum data by performing frequency analysis on the Doppler signals stored in the memory circuit at a prescribed interval.

Referring to FIG. 1, the image data generating unit 5 includes a reference image data generating unit 51, a panoramic image data generating unit 52 and a measured image data generating unit 53. The reference image data generating unit 51 includes a memory circuit (not shown). In a reference mode, B mode image data obtained as reference image data is generated by storing B mode data successively supplied from the B mode data generating unit 41 of the ultrasound data generating unit 4 for the ultrasound transmission/reception directions into the memory circuit of the reference image data generating unit 51.

The panoramic image data generating unit 52 includes an image data connecting unit and an image data memory unit (both are not shown). The image data connecting unit generates a new panoramic image data (a second panoramic image data) by combining a previous panoramic image data (a first panoramic image data) generated based on the acquired reference image and stored in the image data memory unit with the latest reference image data supplied from the reference image data generating unit 51. For instance, in a pattern matching process, a cross-correlation calculation is performed on an overlap area, i.e., an image data area having common image data between the newly acquired reference image data and the first panoramic image data, in order to detect a relative position difference between image data. Based on a result of the detection, the second panoramic image data is generated using the first panoramic image data and position corrected reference image data.

The acquired second panoramic image data is displayed on the display unit 7. In addition, the acquired second panoramic image data is stored in the image data memory unit as new first panoramic image data. Thus, at each time that a position of the ultrasound probe 3 is renewed, the image data connecting unit in the panoramic image data generating unit 52 generates the second panoramic image data based on the reference image data supplied from the reference image data generating unit 51 and the first panoramic image data stored in the image data memory unit.

Figure 5A:
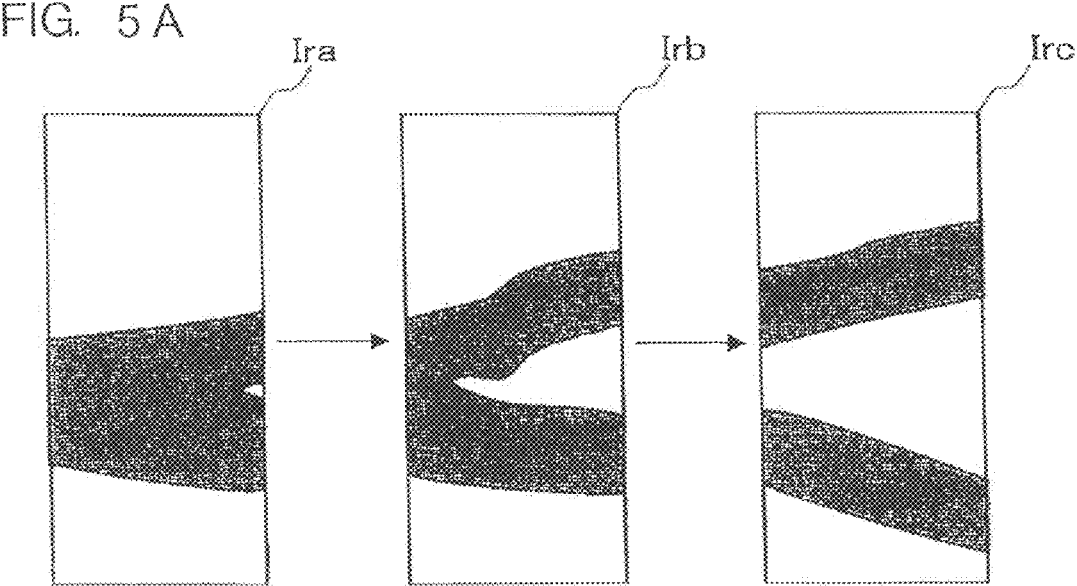
FIGS. 5A and 5B illustrate a method for generating panoramic image data in the ultrasound diagnosis apparatus according to one embodiment of the invention.
Figure 5B:
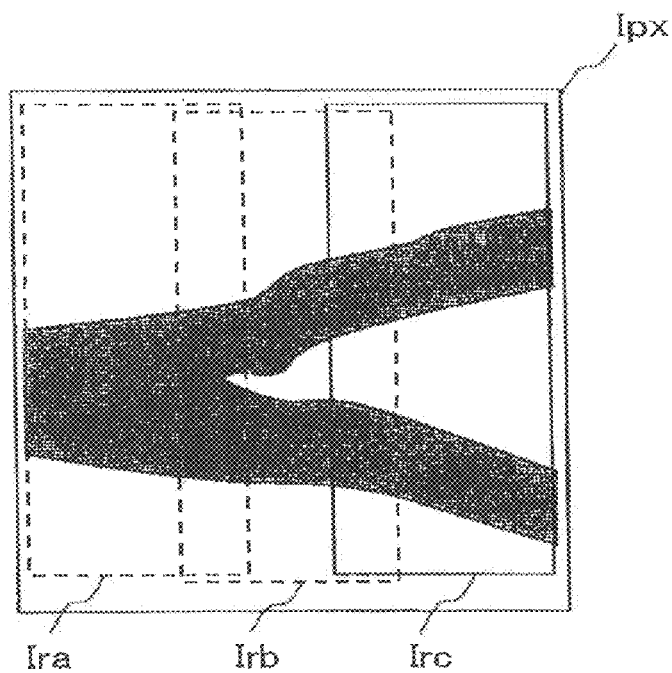

FIGS. 5A and 5B illustrate a method for generating panoramic image data. FIG. 5A illustrates data from three reference images Ira-Irc that is adjacently acquired by moving the ultrasound probe 3 along an array direction of the transducers and touching a neck portion. FIG. 5B illustrates a panoramic image data Ipx generated by combining the data of these three reference images.

In this example, a right-side area of the reference image data Ira and a left-side area of the reference image data Irb, acquired adjacent to the image data Ira, have common image data. Similarly, a right-side area of the reference image data Irb and a left-side area of the reference image data Irc have common image data.

The image data connecting unit in the panoramic image data generating unit 52 detects a relative position difference between the data of the two images by performing a pattern matching process using the acquired reference image data Ira and Irb or using the reference image data Irb and Irc. Based on a result of the detection, panoramic image data is generated by combining the data of the two reference images.

Thus, the reference image data Ira is acquired by touching the ultrasound probe 3 to a diagnosis target region (neck portion) of an object. Once the reference image data Irb and Irc are successively acquired by moving the ultrasound probe 3, the image data connecting unit stores the reference image data Ira supplied from the reference image data generating unit 51 in the image data memory unit as the first panoramic image data. Then, the second panoramic image data is generated based on the reference image data Irb which is newly supplied from the reference image data generating unit 51, a movement of the ultrasound probe 3, and the first panoramic image data, i.e., reference image data Ira, read out from the mage data memory unit. The acquired second panoramic image data is displayed on the display unit 7. Further, the acquired second panoramic image data is stored in the image data memory unit as new first panoramic image data.

Similarly, the image data connecting unit generates the second panoramic image data based on the reference image data Irc supplied from the reference image data generating unit 51 and the first panoramic image data read out from the image data memory unit. The generated second panoramic image data is displayed on the display unit 7. Further, the second panoramic image data is stored in the image data memory unit as new first panoramic image data. By repeating these steps, a broad range panoramic image data Ipx is generated. The latest reference image data constructing the second panoramic image data is displayed on the display unit 7 at any point, e.g., the reference image data in FIG. 5B, is displayed in a substantially real time as a dynamic picture image. In addition, a measurement marker is set up through the input unit 8 at a measuring position of bloodstream data shown by the reference image data.

Turning to FIG. 1, the measured image data generating unit 53 in the image data generating unit 5 detects the maximum frequency fp for each spectrum data that is time sequentially supplied from the spectrum data generating unit 42 at a prescribed time interval. In addition, the image data generating unit 53 generates the spectrum image data indicating temporal changes in the maximum frequency fp as image data.

Figure 6:
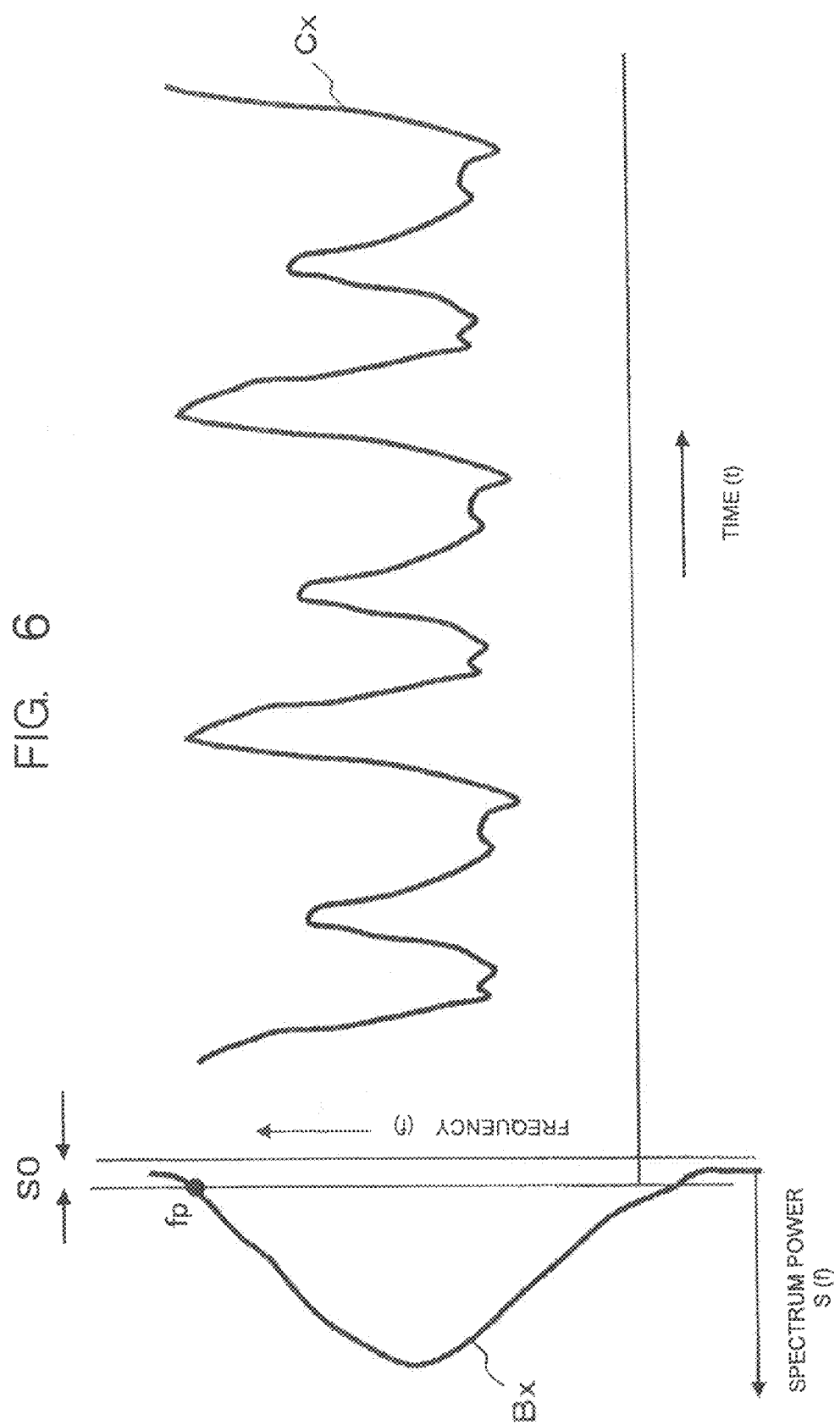
FIG. 6 illustrates an example of image data in the ultrasound diagnosis apparatus according to one embodiment of the invention.

FIG. 6 illustrates an example of the image data generated by the image data generating unit 53. At a left-side portion of the image data, the latest spectrum data Bx generated by the spectrum data generating unit 42 is represented on a longitudinal axis of the frequency (f) and a horizontal axis of the spectrum power S(f). The maximum frequency fp corresponding to the maximum speed of the bloodstream is detected by comparing the spectrum data Bx with a preliminary determined threshold value S0. A trend waveform Cx representing the temporal changes in the detected maximum frequency fp is illustrated at a right-side portion of the image data.

The diagnosis parameters measuring unit 6 (FIG. 1) first receives image data supplied from the image data generating unit 53 in the image data generating unit 5. The diagnosis parameters measuring unit 6 then detects positions (times) of a cardiac peak of systolic (Ps) and an end of diastolic (Ed) by respectively detecting maximum and minimum values of the trend waveform Cx for the maximum frequency fp constructing the image data.

Figure 7:
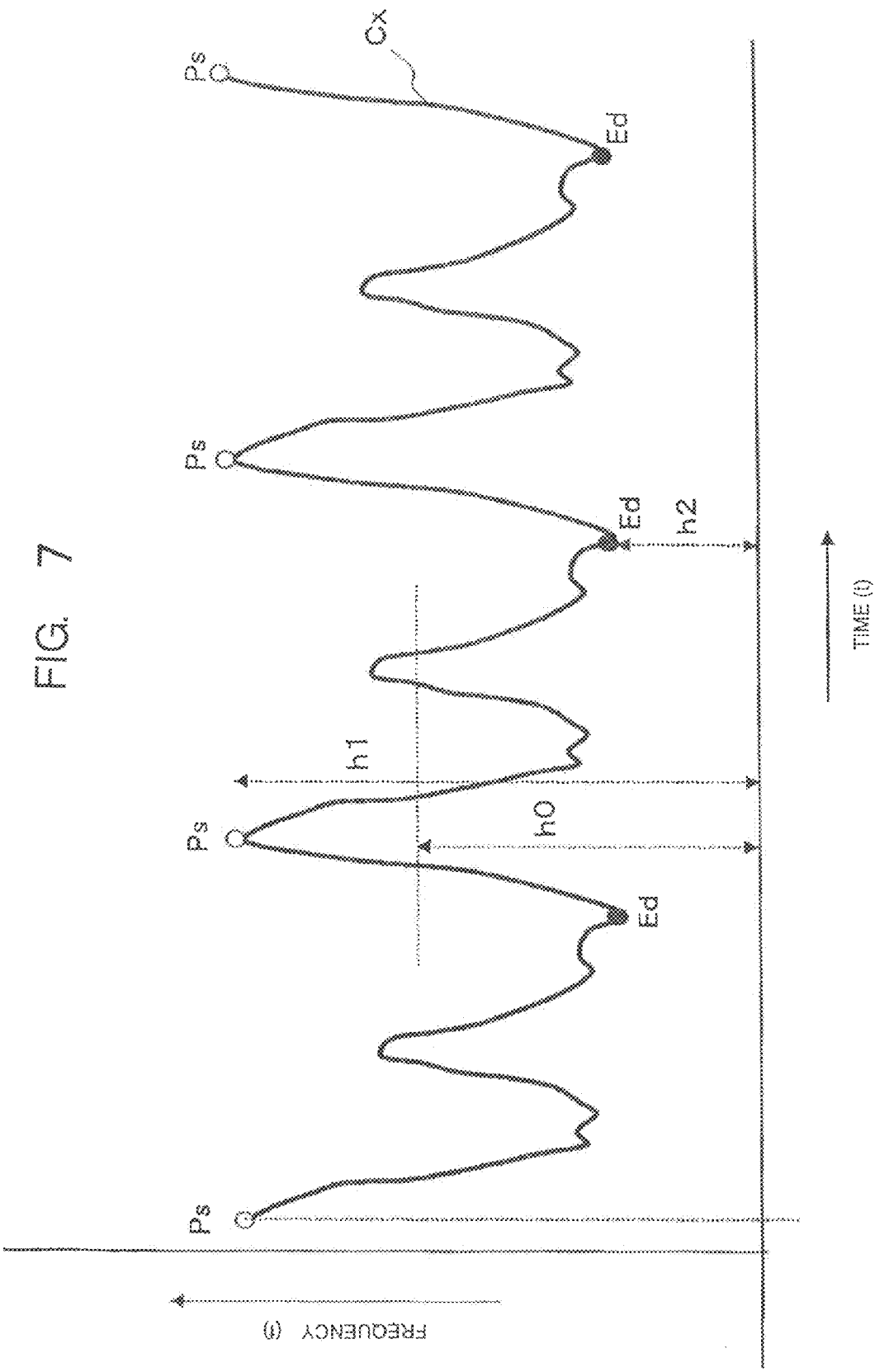
FIG. 7 illustrates a peak of systolic (Ps) and an end of diastolic (Ed) in image data of the ultrasound diagnosis apparatus according to one embodiment of the invention.

FIG. 7 represents the detected cardiac peak of systolic (Ps) and the end of diastolic (Ed) in the trend waveform Cx of the image data. To automatically detect these cardiac peaks of systolic (Ps) and end of diastolic (Ed), while the peaks of systolic (Ps) representing the maximum value are relatively easily detected, it is fairly difficult to detect the end of diastolic (Ed) representing the minimum value. To automatically detect such an end of diastolic (Ed), for instance, the diagnosis parameters measuring unit 6 detects one Ps and a plurality of Ed slate points in one heart rate by using a first differential calculation or a secondary differential calculation that are performed after smoothing the trend waveform Cx to detect inflection points. Further, the end of diastolic (Ed) is detected by selecting one Ed candidate point among the plurality of Ed candidate points located in a prescribed scope to the peak of systolic (Ps).

Based on the maximum frequency fp (ps) at the peak of systolic (Ps) and the maximum frequency fp (ed) at the end of diastolic (Ed), the diagnosis parameters measuring unit 6 measures a maximum bloodstream speed Vps at the peak of systolic (Ps), a maximum bloodstream speed Ved at the end of diastolic (Ed), and a ratio S/D between the maximum frequency Vps and the maximum frequency Ved. The diagnosis parameters measuring unit 6 further measures diagnosis parameters representing dynamic state of blood circulations, such as a heart rate (HR), a pulsatility index (PI) and a resistance index (RI), based on the trend waveform Cx in a period Ps-Ps, if necessary. These PI and RI may be calculated based on the following formula (1).

$$PI = \frac{h1 - h2}{h0} \tag{1}$$

$$RI = \frac{h1 - h2}{h1}$$

Where the value h1 corresponds to the maximum frequency fp (ps) at a peak of systolic (Ps) in the trend waveform Cx, the value h2 corresponds to the maximum frequency fp (ed) at an end of diastolic (Ed) in the trend waveform Cx (see FIGS. 6), and h0 is a mean value of the maximum frequency fp.

The display unit 7 (FIG. 1) includes a data memory unit 71, a display data generating unit 72 and a monitor 73. The data memory unit 71 stores the image data generated by the measured image data generating unit 53 based on reception signals acquired from the bloodstream data measurement position of the object and the measuring results of the diagnosis parameters measured by the diagnosis parameters measuring unit 6 using the image data with the position data of the bloodstream data measurement position as incidental data.

The display data generating unit 72 converts the panoramic image data supplied from the panoramic image data generating unit 52 in the image data generating unit 5 and the image data supplied from the image data generating unit 53 in a prescribed display format for displaying on the monitor 73. In particular, when the input unit 8 inputs a measuring result display command for the diagnosis parameters, the display data generating unit 72 reads out the image data and the diagnosis parameters measuring result stored in the data memory unit 71 and generates display data by placing the image data and the diagnosis parameters measuring result on a broad range panoramic image data supplied from the panoramic image data generating unit 52. The acquired display data is displayed on the monitor 73 by performing data conversion processes, such as an analog-to-digital (A/D) conversion and a display format conversion. For example, the image data and diagnosis parameters measuring results are displayed in correspondence with each of the bloodstream data measurement positions represented by the parameter image data which is based on the position data of bloodstream data measurement position. The bloodstream data measurement positions are displayed in correspondence in a overlapping or parallel arrangement.

FIG. 8 illustrates an example of the generation of displaying data by the display data generating unit 72. The displaying data is generated by composing the panoramic image data Ip generated based on the reference image data Ir1-Ir7, the measured image data Dm1-Dm3 (obtained based on the reference image data Ir1, Ir4 and Ir and Doppler signals acquired from the bloodstream data measuring positions Sv2, Sv4 and Sv7), and the measurement results Cv1-Cv3 of the diagnosis parameters Vps, Ved and S/D that are measured based on the measured image data.

In FIG. 8, the generation of image data at the bloodstream data measurement positions Sv2, Sv4 and Sv7, and the measurements of diagnosis parameters are performed by monitoring the reference image data Ir2, Ir4 and Ir7 displayed in a real time. On each of the bloodstream data measuring positions Sv2, Sv4 and Sv7, a range gate marker (•) for indicating a position of the range gate set up by the input unit 8, and a scan line marker (dashed-dotted line) for indicating the reception direction at the respective bloodstream data measuring position are overlapped as measurement markers.

The input unit 8 shown in FIG. 1 includes various input devices, such as a display panel, keyboard, trackball, mouse, and selection buttons on an operation panel. By selectively using these devices, the input unit 8 is able to, among other things, a) input object data, b) set up generating conditions for the reference image data, the panoramic image data, and the image data, c) designate bloodstream data measurement positions for the panoramic image data, d) set up ultrasound transmission/reception directions θd in the measurement mode, e) select the reference mode and the measurement mode, and d) input various command signals.

The scan control unit 9 shown in FIG. 1 supplies element selection control signals to the elements selection unit 21 in the transmission/reception unit 2 for controlling both the ultrasound transmission/reception direction (FIG. 3A) in the reference mode (which is used to generate the reference image data) and the ultrasound transmission/reception direction (FIG. 3B) in the measurement mode (which is used to generate the image data). Further, the scan control unit 9 supplies delay time control signals to the transmission delay circuit 222 in the transmission unit 22 and the reception delay circuit 233 in the reception unit 23.

The system control unit 11 includes a central processing unit (CPU) and a memory circuit (both are not shown). The data inputted, set up, selected or designated through the input unit 8 is stored in the memory circuit. Based on this data, the CPU is able to fully control each of the units included in the ultrasound diagnosis apparatus 100 and the total system. The system control unit 11 controls the generation of the reference image data in the reference mode, the panoramic image data by combining adjoining acquired reference image data, and the image data at the bloodstream data measurement positions in the panoramic image data, and controls the measurement of various diagnosis parameters based on the image data.

Figure 9:
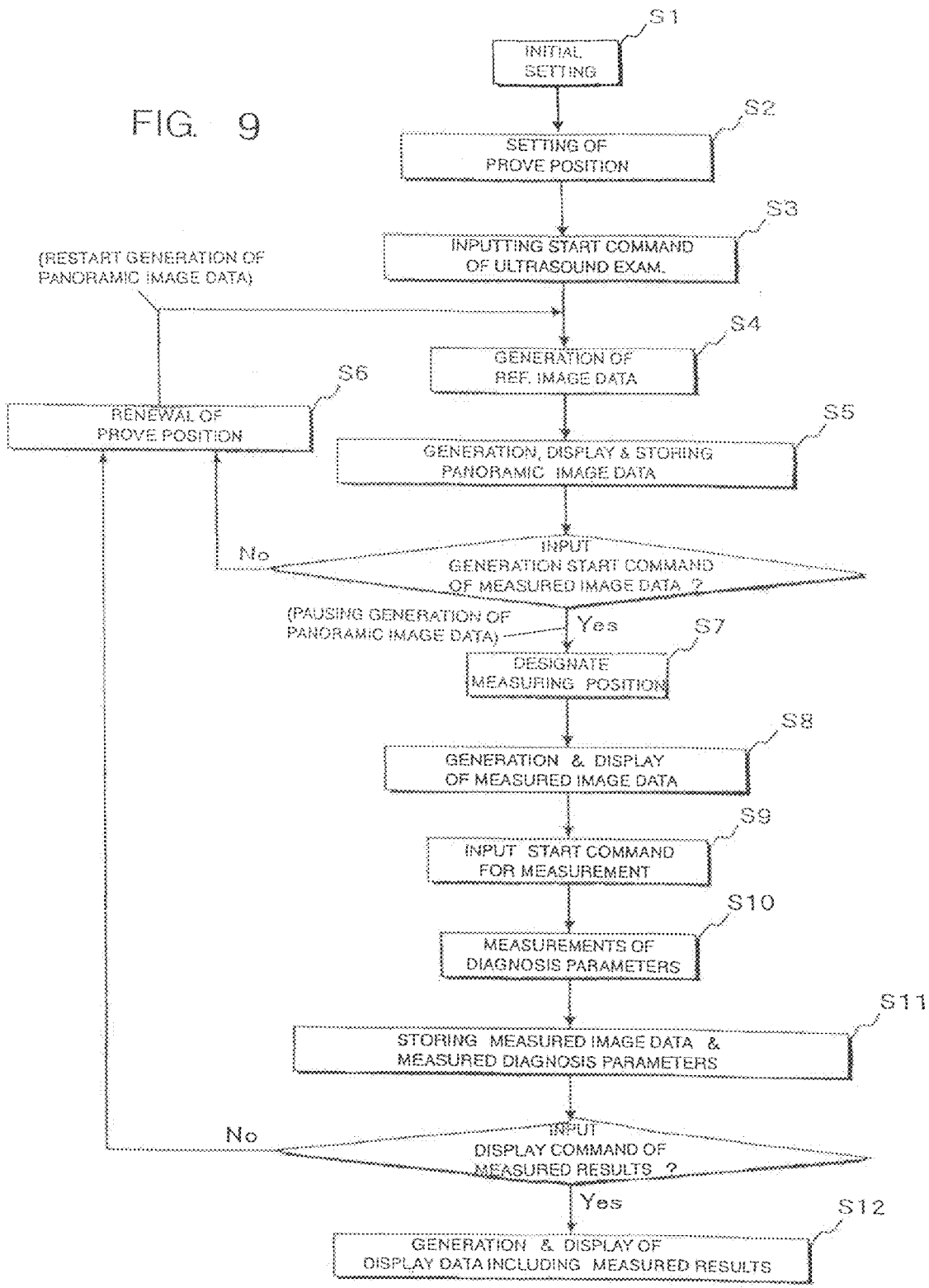
FIG. 9 is a flowchart illustrating displaying diagnosis parameter measuring results in the ultrasound diagnosis apparatus according to one embodiment of the invention.

FIG. 9 is a flowchart illustrating the process of displaying the diagnosis parameters measuring result according to an embodiment of the present invention. As illustrated in FIG. 8, the panoramic image data Ip generated based on the reference image data Ir1-Ir7, the image data Dm1-Dm3 at the bloodstream data measurement positions Sv2, Sv4 and Sv7 displayed in the panoramic image data Ip, and the measuring results Cv1-Cv3 of the diagnosis parameters measured based on the image data, are respectively displayed in a corresponding manner. In addition, the total sheet number of reference image data and the number of bloodstream data measurement positions are not limited.

Prior to the start of ultrasound examinations on an examining target portion, e.g. a neck region, of an object, an operator of the ultrasound diagnosis apparatus 100 performs initial settings through the input unit 8. Thus, object data, conditions for generating reference image data and panoramic image data are inputted. The generating conditions of image data and ultrasound transmission/reception direction θd in the measurement mode are set up. Further, the reference mode is selected through the input unit 8. In addition, this initially set up data is stored in the memory circuit of the system control unit 11 (FIG. 9, step S1). After placing the ultrasound probe 3 at a first position of an examination target region (FIG. 9, step S2), an ultrasound examination start command is input through the input unit 8 (FIG. 9, step S3).

The scan control unit 9 receives the command signal from the input unit 8 through the system control unit 11, and performs ultrasound transmissions/receptions on the object by controlling the elements selection unit 21, the transmission delay circuit 222 and the reception delay circuit 233 in the transmission/reception unit 2 based on the reference mode scan control program stored in the memory circuit.

The B mode data generating unit 41 in the ultrasound data generating unit 4 then generates B mode data by processing receiption signals acquired through the ultrasound transmissions and receptions. The reference image data generating unit 51 in the image data generating unit 5 generates a reference image data Ir1 by storing B mode data that is time sequentially supplied from the B mode data generating unit 41 in correspondence with the ultrasound transmission/reception directions stored in the memory circuit (FIG. 9, step S4).

Then, the image data connecting unit in the panoramic image data generating unit 52 stores the reference image data Ir1 supplied from the reference image data generating unit 51 in the image data memory unit as first panoramic image data. At the same time, the reference image data Ir1 is displayed on a monitor 73 in the display unit 7 (FIG. 9, step S5).

When a bloodstream data measurement position is not observed in the panoramic image data by monitoring the first panoramic image data, i.e. reference image data Ir1, displayed on the display unit 7, the operator moves the ultrasound probe 3 along an array direction of the transducers for performing ultrasound transmissions and receptions in a new reference mode at a renewed position on the target region (FIG. 9, step S6).

The reference image data generating unit 51 in the image data generating unit 5 generates reference image data Ir2 using the B mode data of receiving signals acquired through the ultrasound transmissions and receptions (FIG. 9, step S4). The image data connecting unit in the panoramic image data generating unit 52 generates a second parameter image data by combining the reference image data Ir2 supplied from the reference image data generating unit 51 with the first panoramic image data, i.e., reference image data Ir1, read out from the image data memory unit. The generated second parameter image data is then displayed on the monitor 73 in the display unit 7. Further the second parameter image data is stored in the image data memory unit as the first panoramic image data (FIG. 9, step S5).

After confirming a bloodstream data measurement position Sv2 in the panoramic image data displayed on the display unit 7, the operator sets up the measurement mode and inputs a start command for generating measured image data through the input unit 8. Based on the start command, a measurement marker placed on the panoramic image data is moved to a bloodstream data measurement position Sv2. By moving the measurement marker placed on the panoramic image data, the measurement position Sv2 of the bloodstream data is designated on the panoramic image data (FIG. 9, step S7).

After receiving the measurement marker position data and the set up data of a measurement mode, the scan control unit 9 alternately performs ultrasound transmissions and receptions in both the reference mode (shown in FIG. 3) and the measurement mode by controlling the elements selection unit 21 in the transmission/reception unit 2 and both the transmission delay circuit 222 and the reception delay circuit 233. The receiving signals acquired through the ultrasound transmissions and receptions in the reference mode are processed by steps S4 and S5 to generate panoramic image data. The generated panoramic image data is stored in the image data memory unit of the panoramic image data generating unit 52. Further, the generated panoramic image data is displayed on the monitor 73 in the display unit 7. The displayed panoramic image data is constructed from the reference image data Ir1 displayed as a static image and the reference image data Ir2 displayed as a dynamic picture image. A measurement marker set up on the bloodstream data measurement position Sv2 is placed on the reference image data Ir2 displayed substantially in real time.

The spectrum data generating unit 42 in the ultrasound data generating unit 4 receives the receiving signals acquired through the ultrasound transmissions and receptions in the measurement mode. By orthogonally phase detecting the receiving signals, Doppler signals are detected. By performing a frequency analysis of the acquired Doppler signals, spectrum data is generated. The measured image data generating unit 53 in the image data generating unit 5 detects a maximum frequency fp of the spectrum data sequentially supplied at a prescribed time interval from the spectrum data generating unit 42 in order to generate spectrum image data (measured image data) indicating temporal alternation of the maximum frequency fp. The image data is displayed on the display unit 7 (FIG. 9, step S8).

Once the image data is confirmed on the display unit 7 as being normally generated, the operator inputs a command for starting diagnosis parameter measurement through the input unit 8 (FIG. 9, step S9). The start command signal is supplied to the diagnosis parameters measuring unit 6 through the system control unit 11. The diagnosis parameters measuring unit 6 measures various diagnosis parameters based on the trend waveform of the maximum frequency fp of the image data supplied from the measured image data generating unit 53 (FIG. 9, step S10). The measured image data acquired at step S8 and the measurement results of diagnosis parameters acquired at step S10 are stored in the data memory unit 71 provided in the display unit 7. In addition, the position data of the bloodstream data measurement position Sv2 is attached in the storage as an incidental data (FIG. 9, step S11).

The acquisitions of the reference image data upon renewal of ultrasound probe positions are continued until a display command of the diagnosis parameters measuring result is input through the input unit 8. For instance, as illustrated in FIG. 8, when the reference image data Ir4 is newly generated, the generation of panoramic image data constructed by the reference image data Ir1 to Ir4 and the display of the panoramic image data is performed by the steps S4 through S6. The generation of the image data corresponding to the bloodstream data measurement position Sv4 and the measurement of diagnosis parameters indicated by the panoramic image data are performed by the steps S7 through S10.

Similarly, when the reference image data Ir1 is newly generated, the generation and display of the panoramic image data constructed by the reference image data Ir1 to Ir7 are performed in the steps S4 through S6. Generation of the measured image data at the bloodstream data measurement position Sv7 indicated by the panoramic image data and measurement of diagnosis parameters are performed in the steps S7 through S10. The image data generated at step S8 and the measurement results of the diagnosis parameters acquired at step S10 are stored in the data memory unit 71 of the display unit 7 with the position data of the bloodstream data measurement positions Sv4 and Sv7 attached as incidental data (FIG. 9, steps S4 through S11).

When the reference image data Ir3 is newly generated, only the generation and display of panoramic image data constructed by the reference image data Ir1 to Ir3 are performed in steps S4 through S6. Similarly, when the reference image data Ir5 or the reference image data Ir6 is newly generated, only the generation and display of panoramic image data constructed by the reference image data Ir1 to Ir5 or the reference image data Ir1 to Ir6 are performed in steps S4 through S6.

When the diagnosis parameter measurements at each of the bloodstream data measurement positions Sv2, Sv4 and Sv7 have finished, the operator inputs a display command for the measured results of the diagnosis parameters through the input unit 8. Upon receiving the displaying command through the system control unit 11, the display data generating unit 72 reads out the measured image data and the measured diagnosis parameters at each of the bloodstream data measurement positions Sv2, Sv4 and Sv7 from the data memory unit 71. The display data generating unit 72 further creates the broad range panoramic image data Ip from the reference image data Ir1 to Ir7 supplied from the panoramic image data generating unit 52 with each of the measured image data and the measured diagnosis parameters for generating the displaying data. The acquired display data is then displayed on the monitor 73 by performing data conversion processes, such as A/D conversions or display format conversions (FIG. 9, step S12).

According to an embodiment of the present invention, it is possible to easily and accurately generate the measured image data at each of the plurality of bloodstream data measurement positions indicated by the panoramic image data. Further, the diagnosis parameters can be measured by monitoring and the panoramic image data can be displayed in a broader range. Thus, the accuracy and efficiency of the examination can be largely improved. Further, the burden to the operator in the ultrasound examination can be reduced.

In particular, according to the above-mentioned embodiment, the plurality of bloodstream data measurement positions indicated in the panoramic image data, the measured image data generated based on Doppler signals acquired at the bloodstream data measurement positions and the measurement results of the various diagnosis parameters acquired by using the image data can be displayed in correspondence with each other. Thus, as a result, it is possible to review diagnosic data in a short time.

According to the embodiment consistent with the present invention, the latest reference image data constructing the panoramic image data can be displayed as the dynamic picture image in a real time. And, since the latest bloodstream data measurement positions can be designated based on the latest reference image data, is plurality of bloodstream data measurement positions can be easily and accurately designated.

The present invention is not limited to the above-mentioned embodiments. For instance, while the B mode image data is generated as the reference image data, and the spectrum image data is generated as the measured image data in the above-mentioned embodiment, color Doppler image data or color B mode image data overlapped with the Doppler image data can also be used as the reference image data. Further, it is also possible to use the spectrum image data representing the temporal alternation of the spectrum data as the measured image data. It is also possible to apply the M mode image data representing the temporal alternation of B mode data.

In the above-mentioned embodiments, the panoramic image data is continuously generated by connecting a plurality of frames. Of course, it is also possible to pause and restart the generation of the panoramic image data. Thus, the generation of the panoramic image data can be paused to acquire the reference image data of Doppler mode or M mode. And when the acquisition of the reference image data has completed, the generation of the panoramic image data can be restarted at the point of the panoramic image data acquired before pausing.

Further, in the above-mentioned embodiment, the reference image data and the panoramic image data are exemplary explained as a two dimensional (2D) data. Of course, the present invention can be applied to three dimensional (3D) reference image data and 3D panoramic image data.

Of course, the diagnosis target region for measuring the bloodstream data is not limited to an arterial carotis in a neck portion of an object but the bloodstream data in other portions or organs also can be measured. Further, the measurement itself is not limited to the diagnosis parameter or the bloodstream data.

In the embodiment, the latest reference image data constructing the panoramic image data is displayed as a dynamic picture image in a real time. It is also possible to display the latest reference image data as a static image similar to the other reference image data constructing the panoramic image data.

In the above-mentioned embodiment, the image data generating unit 53 detects the maximum frequency fp of spectrum data supplied from the spectrum data generating unit 42 and generates measured image data (spectrum image data) based on temporal alternation of the maximum frequency fp. It is also possible to detect a central frequency fc of the spectrum data and to generate the measured image data based on temporal alternation of the central frequency fc. A mean frequency fc of this case can be acquired through the following formula (2) by supposing that S(fc) is a spectrum power at the frequency fs.

$$fc = \frac{\sum_{s=1}^{m} f_s S(f_s)}{\sum_{s=1}^{m} S(f_s)} \quad (2)$$

Other embodiments consistent with the present invention will be apparent to those skilled in the art from consideration of the specification and practice of the present invention disclosed herein. It is intended that the specification and examples be considered as exemplary only, with the true scope and spirit of the present invention being indicated by the following claims.

The invention claimed is:

1. An ultrasound image diagnosis apparatus for measuring diagnosis parameters based on image data acquired through ultrasound transmissions and receptions along prescribed directions with respect to an object, the ultrasound image diagnosis apparatus comprising:
   an ultrasound probe including a plurality of transducers configured to transmit and receive ultrasound pulses and ultrasound echo waves to and from the object;
   a transmission/reception unit configured to supply driving signals to the plurality of transducers for transmitting the ultrasound pulses along the prescribed directions and to perform phase compensation/summation on a plurality of reception signals acquired from the plurality of transducers;
   an ultrasound data generating unit implemented by processing circuitry and configured to generate both ultrasound data in a reference mode and ultrasound data in a measurement mode by processing the phase compensated/summed receiving signals;
   a reference image data generating unit configured to generate reference image data based on ultrasound data in the reference mode acquired through ultrasound transmission/reception along the prescribed directions with respect to the object;
   a panoramic image data generating unit configured to generate panoramic image data by combining a plurality of reference image data successively generated from the reference image data generating unit;
   a diagnosis parameters measuring unit implemented by the circuitry configured to measure diagnosis parameters based on ultrasound data in the measurement mode acquired through ultrasound transmission/reception at a plurality of measurement positions designated in the panoramic image data;
   a non-transitory memory configured to store measured results of the diagnosis parameters incidental with position data of the plurality of measurement positions;
   a display data generating unit implemented by the circuity configured to generate display data by overlapping measurement markers on the panoramic image data based on the position data and the measured results stored in the memory at positions corresponding to the measurement markers; and
   a display unit configured to display the panoramic image data correlated with at least one of a measured image data and the measured results of the diagnosis parameters in a corresponding manner.

2. The ultrasound image diagnosis apparatus according to claim 1, further comprising
   a measurement position designating unit configured to designate the measurement position on a latest reference image data composing the panoramic image data; and
   wherein the measured image data generating unit generates the measured image data based on the ultrasound data of the measurement mode generated by the ultrasound data generating unit for the ultrasound transmissions/receptions at the designated measurement position.

3. The ultrasound image diagnosis apparatus according to claim 1, wherein the reference image data generating unit generates at least one of B mode image data or color Doppler image data as the reference image data based on the ultrasound data of the reference mode supplied from the ultrasound data generating unit.

4. The ultrasound image diagnosis apparatus according to claim 1, wherein the ultrasound probe includes functions for receiving three dimensional (3D) data; and
   the reference image data generating unit generates three dimensional (3D) reference image data based on the 3D receiving data.

5. The ultrasound image diagnosis apparatus according to claim 1, wherein the measured image data generating unit generates at least either one of spectrum image data or M mode image data as the image data based on the ultrasound data of the measurement mode supplied from the ultrasound data generating unit.

6. The ultrasound image diagnosis apparatus according to claim 1, wherein the panoramic image data generating unit detects positional differences among reference image data which adjoin along a time axis direction and have common image data at respective edge portions, and generates the panoramic image data by combining the reference image data based on a result of the detection.

7. The ultrasound image diagnosis apparatus according to claim 1, wherein the panoramic image data generating unit detects positional differences among a plurality of three dimensional (3D) reference image data which adjoin along a time axis direction and have common image data at respective edge portions, and generates three dimensional (3D) panoramic image data by combining the plurality of reference image data based on a result of the detection.

8. The ultrasound image diagnosis apparatus according to claim 1, wherein the panoramic image data generating unit, implemented by the processing circuitry, is configured to temporally pause the generation of the panoramic image data when a start command for the measured image data is received and restart the generation of the panoramic image data when the generation of the measured image data is finished continuing with the panoramic image data generated before the pausing.

9. The ultrasound image diagnosis apparatus according to claim 4, wherein the diagnosis parameters measuring unit measures, based on the spectrum image data supplied from the image data generating unit, at least one of a bloodstream speed at a peak of systolic (Ps) of a heart, a bloodstream speed at an end of diastolic (Ed) of a heart, a bloodstream speed ratio Ps/Ed, a pulsatility index (PI) and an Resistance Index (RI), as the diagnosis parameter.

10. The ultrasound image diagnosis apparatus according to claim 2, wherein the display unit is further configured to display at least one of: the measured image data generated at each of the plurality of measurement positions designated by the measurement position designating unit, and the measured results of diagnosis parameters obtained based on the measured image data corresponding to the measurement positions designated in the panoramic image data.

11. The ultrasound image diagnosis apparatus according to claim 7, wherein the display unit is further configured to display a measurement marker indicating the measurement position, the marker displayed in an overlapping manner on the panoramic image data.

12. A control method for measuring diagnosis parameters in an ultrasound image diagnosis apparatus that measures diagnosis parameters based on image data acquired through ultrasound transmission/reception along prescribed directions with respect to an object, the measurement controlling method comprising:
supplying driving signals to a plurality of transducers in an ultrasound probe that transmits ultrasound pulses along the prescribed directions;
performing phase compensation/summation on a plurality of receiving signals acquired from the plurality of transducers;
generating both ultrasound data in a reference mode and ultrasound data in a measurement mode by processing the phase compensated/summed receiving signals;
generating reference image data based on ultrasound data obtained in the reference mode acquired through ultrasound transmission/reception along the directions with respect to the object;
generating panoramic image data by combining a plurality of the reference image data successively generated by the generating reference image data;
measuring diagnosis parameters based on ultrasound data in the measurement mode acquired through ultrasound transmission/reception at a plurality of measurement positions designated in the panoramic image data;
storing measured results of the diagnosis parameters incidental with position data of the plurality of measurement positions;
generating display data by overlapping measurement markers on the panoramic image data based on the position data and the measured results stored by the storing at positions corresponding to the measurement markers;
generating separate measured image data for a plurality of measurement positions based on ultrasound data acquired in the measurement mode through ultrasound transmission/reception at the plurality of measurement positions designated in the panoramic image data; and
displaying the panoramic image data correlated with at least one of the measured image data in a corresponding manner, the displaying further displaying each of the separate measured image data at different positions.

13. The controlling method for measuring diagnosis parameters of an ultrasound image diagnosis apparatus according to claim 12, wherein
the generation of the panoramic image data is temporally paused when a start command for the measured image data is received and is restarted when the generation of the measured image data is finished continuing with the panoramic image data generated before pausing.

14. An ultrasound image diagnosis apparatus for measuring diagnosis parameters based on image data acquired through ultrasound transmissions and receptions along prescribed directions with respect to an object, the ultrasound image diagnosis apparatus comprising:
an ultrasound probe including a plurality of transducers configured to transmit and receive ultrasound pulses and ultrasound echo waves to and from the object;
a transmission/reception unit configured to supply driving signals to the plurality of transducers for transmitting the ultrasound pulses along the prescribed directions and to perform phase compensation/summation on a plurality of reception signals acquired from the plurality of transducers;
an ultrasound data generating unit implemented by processing circuitry configured to generate both ultrasound data in a reference mode and ultrasound data in a measurement mode by processing the phase compensated/summed receiving signals;
a reference image data generating unit implemented by the processing circuitry configured to generate reference image data based on ultrasound data in the reference mode acquired through ultrasound transmission/reception along the prescribed directions with respect to the object;
a panoramic image data generating unit implemented by the processing circuitry configured to generate a panoramic image data by combining a plurality of reference image data successively generated from the reference image data generating unit;
a measured image data generating unit implemented by the processing circuitry configured to generate Doppler spectrum data based on ultrasound data in the measurement mode acquired through ultrasound transmission/reception at a plurality of measurement positions designated in the panoramic image data;
a non-transitory memory configured to store the Doppler spectrum data incidental with position data of the plurality of measurement positions;
a display data generating unit implemented by the processing circuitry configured to generate display data by overlapping measurement markers on the panoramic image data based on the position data and the measured results stored in the memory at positions corresponding to the measurement markers; and a display unit configured to display the panoramic image data correlated with at least one of a measured image data and the measured results of the diagnosis parameters in a corresponding manner.

\* \* \* \* \*